United States Patent
Baumann et al.

[11] Patent Number: 4,981,962
[45] Date of Patent: Jan. 1, 1991

[54] SUBSTITUTED TETRATHIOTETRACENES AND TETRASELENOTETRACENES

[75] Inventors: Marcus Baumann, Basel; Walter Fischer; Vratislav Kvita, both of Reinach; Carl W. Mayer, Riehen, all of Switzerland; Wolfgang Wernet, Freiburg, Fed. Rep. of Germany

[73] Assignee: Ciba-Geigy Corporation, Ardsley, N.Y.

[21] Appl. No.: 356,824

[22] Filed: May 24, 1989

[30] Foreign Application Priority Data

May 27, 1988 [CH] Switzerland .................. 2008/88
Jul. 19, 1988 [CH] Switzerland .................. 2752/88

[51] Int. Cl.$^5$ .............. C07D 345/00; C07D 339/04; C07D 295/116; C07D 211/74
[52] U.S. Cl. ........................... 540/1; 544/96; 544/378; 549/4; 549/31; 548/406; 548/526; 546/14; 546/197
[58] Field of Search ............ 549/31, 4; 546/197, 546/14; 544/378, 96; 548/526, 406; 540/1

[56] References Cited

U.S. PATENT DOCUMENTS

| 4,522,754 | 6/1985 | Hilti et al. ............... 260/239 R |
| 4,601,853 | 7/1986 | Hilti et al. ............... 260/239 R |
| 4,617,151 | 10/1986 | Mayer et al. .............. 540/1 |
| 4,801,701 | 1/1989 | Hilti et al. ............... 540/1 |

OTHER PUBLICATIONS

Chem. Abstr., vol. 86: 189773u (1977).
Chem. Abstr., vol. 99: 175630b (1983).
Chem. Abstr., vol. 103: 225177h (1985).

*Primary Examiner*—Mary C. Lee
*Assistant Examiner*—Jacqueline Haley
*Attorney, Agent, or Firm*—Michael W. Glynn; Stephen V. O'Brien

[57] ABSTRACT

Substituted tetrathiotetracenes and tetraselenotetracenes of the formula I

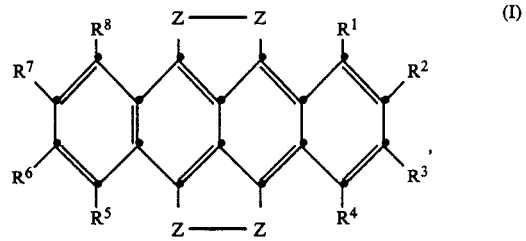

in which Z is —S— or —Se— and (a) $R^1$, $R^2$, $R^3$ and $R^4$ are H and $R^5$ to $R^8$ are each H and at least one of the radicals $R^5$ to $R^8$ independently of one another is a substituent belonging to the group comprising $C_1$-$C_{20}$alkyl-$(X)_p$ which is unsubstituted or substituted by halogen, —CN, —CONR$^9$R$^{10}$, —OR$^9$, —SR$^9$ or —COOR$^9$, with the exception of $C_1$-$C_4$alkyl and methoxy, $C_2$-$C_{18}$alkenyl-$(X)_p$, $C_2$-$C_{18}$-alkynyl-$(X)_p$, $C_3$-$C_8$cycloalkyl-$(X)_p$, ($C_1$-$C_{12}$alkyl)—$C_3$-$C_8$cycloalkyl-$(X)_p$, $C_3$-$C_8$cycloalkyl-$C_rH_{2r}$-$(X)_p$, ($C_1$-$C_{12}$alkyl)-$C_3$-$C_8$-cyclo alkyl-$C_rH_{2r}$-$(X)_p$, phenyl-$(X)_p$, ($C_1$-$C_{12}$)alkyl)-phenyl-$(X)_p$, phenyl-$C_rH_{2r}$-$(X)_p$ and ($C_1$-$C_{12}$alkyl)-phenyl-$C_rH_{2r}$-$(X)_p$, r is 1 or 2 and p is 0 or 1 and X is —O—, —S—, —SO— or —SO$_2$—, or $R^5$ to $R^8$ independently are a substituent belonging to the group comprising —Br, —CF$_3$, —CN, —Si($C_1$-$C_4$alkyl)$_3$, —S—($C_mH_{2m}$O)—$_nR^{11}$ or —O-($C_mH_{2m}$O)-$_nR^{11}$, or each one of $R^5$ to $R^8$ is —F or —Cl and at least one further member of $R^5$ to $R^8$ is a substituent of the groups defined above, including $C_1$-$C_4$alkyl and methoxy, $R^9$ and $R^{10}$ independently of one another are H, $C_1$-$C_{12}$alkyl, phenyl or —($C_mH_{2m}$—O)-$_qR^{11}$, or $R^9$ and $R^{10}$ together are tetramethylene, pentamethylene, 3-oxapentylene or —CH$_2$CH$_2$NR$^9$CH$_2$CH$_2$—, $R^{11}$ is H or $C_1$-$C_{12}$-alkyl, m is a number from 2 to 4, n is a number from 2 to 20 and q is a number from 1 to 20, or b) $R^1$ to $R^8$ independently of one another are H or one of the substituents defined above, including $C_1$-$C_4$alkyl and methoxy, or —COOR$^9$ or —CONR$^9$R$^{10}$ or two pairs of adjacent radicals of $R^1$ to $R^8$ are —CO—O—CO— or —CO—NR$^9$—CO—, and at least one of $R^1$ to $R^4$ and also $R^5$ to $R^8$ is a substituent, with the exception of $R^2$, $R^3$, $R^6$ and $R^7$ when these are —F and methyl, and where $R^9$ and $R^{10}$ are as defined above.

With electron acceptors they form charge-transfer complexes which can be used as organic electrical conductors, displays, optical switches and sensors.

12 Claims, No Drawings

SUBSTITUTED TETRATHIOTETRACENES AND TETRASELENOTETRACENES

The invention relates to substituted tetrathiotetracenes and tetraselenotetracenes and to a process for their preparation.

It is known that monofluorotetrathiotetracenes, difluorotetrathiotetracenes, monofluorotetraselenotetracenes and difluorotetraselenotetracenes and tetrathiotetracene-monocarboxylic and -dicarboxylic acids and acid esters and -carboxamides and tetraselenotetracene-monocarboxylic and -dicarboxylic acids and acid esters and -carboxamides form electrically conductive charge-transfer complexes with electron acceptors, see, for example, U.S. Pat. No. 4,522,754, EP-A No. 0,153,905, U.S. Pat. No. 4,617,151 and DE-A No. 3,635,124.

It is reported in CA 103:225177h (1985) that crystals of di(tetrathiotetracene) triiodide can be doped with methoxytetrathiotetracene and ICl. Isopropyltetrathiotetracene is described in CA 86:189773n (1977). Tertiary-butyltetrathiotetracene is described as a constituent of a cation/free-radical salt in CA 99:175630b (1983). The preparation of these substituted chalcogenated tetracenes is associated with involved syntheses.

The invention relates to compounds of the formula I

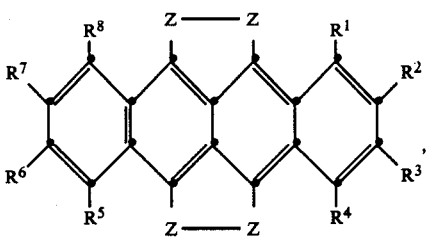

in which Z is -S- or -Se- and (a) $R^1$, $R^2$, $R^3$ and $R^4$ are H and $R^5$ to $R^8$ are each H and at least one of the radicals $R^5$ to $R^8$ independently of one another is a substituent belonging to the group comprising $C_1$-$C_{20}$alkyl-$(X)_p$-which is unsubstituted or substituted by halogen, -CN, -CONR$^9$R$^{10}$, -OR$^9$, -SR$^9$ or -COOR$^9$, with the exception of $C_1$-$C_4$alkyl and methoxy, $C_2$-$C_{18}$alkenyl-$(X)_p$-, $C_2$-$C_{18}$alkynyl-$(X)_p$-, $C_3$-$C_8$cycloalkyl-$(X)_p$-, ($C_1$-$C_{12}$alkyl)-$C_3$-$C_8$cycloalkyl-$(X)_p$-, $C_3$-$C_8$cycloalkyl-$C_rH_{2r}$-$(X)_p$-, ($C_1$-$C_{12}$alkyl)-$C_3$-$C_8$cycloalkyl-$C_rH_{2r}$-$(X)_p$-, phenyl-$(X)_p$-, ($C_1$-$C_{12}$alkyl)phenyl-$(X)_p$-, phenyl-$C_rH_{2r}$-$(X)_p$- and ($C_1$-$C_{12}$-alkyl)phenyl-$C_rH_{2r}$-$(X)_p$-, r is 1 or 2 and p is 0 or 1 and X is -O-, -S-, -SO- or -SO$_2$-, or $R^5$ to $R^8$ independently are a substituent belonging to the group comprising -Br, -CF$_3$, -CN, -Si($C_1$-$C_4$alkyl)$_3$, -S-($C_mH_{2m}$-O)$_n$R$^{11}$ or -O-($C_mH_{2m}$-O)$_n$R$^{11}$, or each one of $R^5$ to $R^8$ is -F or -Cl and at least one further member of $R^5$ to $R^8$ is a substituent of the groups defined above, including $C_1$-$C_4$alkyl and methoxy, $R^9$ and $R^{10}$ independently of one another are H, $C_1$-$C_{12}$alkyl, phenyl or -$C_mH_{2m}$-O)$_qR^{11}$, or $R^9$ and $R^{10}$ together are tetramethylene, pentamethylene, 3-oxapentylene or -CH$_2$CH$_2$NRCH$_2$CH$_2$-, R$^{11}$ is H or $C_1$-$C_{12}$alkyl, m is a number from 2 to 4, n is a number from 2 to 20 and q is a number from 1 to 20, or (b) $R^1$ to $R^8$ independently of one another are H or one of the substituents defined above, including $C_1$-$C_4$alkyl and methoxy, or -COOR$^9$ or -CONR$^9$R$^{10}$ or two pairs of adjacent radicals of $R^1$ to $R^8$ are -CO-O-CO- or -CO-NR$^9$-CO-, and at least one of $R^1$ to $R^4$ and also $R^5$ to $R^8$ is a substituent, with the exception of $R^2$, $R^3$, $R^6$ and $R^7$ when these are -F and methyl, and where $R^9$ and $R^{10}$ are as defined above.

If, within the scope of the preceding definitions, $R^1$ to $R^8$ are $C_1$-$C_{20}$alkyl-$(X)_p$, the alkyl group can be linear or branched and preferably contains 1 to 18, particularly 1 to 12 and especially 1 to 6, C atoms. Examples of alkyl groups are methyl, ethyl and the isomers of propyl, butyl, pentyl, hexyl, heptyl, octyl, octyl, nonyl, decyl, undecyl, dodecyl, tridecyl, tetradecyl, pentadecyl, hexadecyl, heptadecyl, octadecyl and eicosyl. X is preferably -O-, -S- and -SO$_2$- and p is preferably 1.

If, within the scope of the preceding definitions, $R^1$ to $R^8$ are $C_2$-$C_{18}$alkenyl-$(X)_p$, the alkenyl group can be linear or branched and can preferably contain 3 to 12, particularly 3 to 6, C atoms. The alkenyl group preferably contains terminal double bonds. Some examples are ethenyl, allyl, prop-1-en-1-yl, prop-1-en-2-yl, but-1-en-1- or -2- or -3- or -4-yl, but-2-en-1-yl, but-2-en-2-yl, pent-1-en-1- or -2- or -3- or -4-or -5-yl, pent-2-en-1- or -2- or -3- or -4- or -5-yl, hex-1-en-1- or -2- or -3- or -4- or -5- or -6-yl, hex-2-en-1- or -2- or -3- or -4- or -5- or -6-yl, hex-3-en-1- or -2- or -3- or -4- or -5- or -6-yl, heptenyl, octenyl, nonenyl, decenyl, undecenyl, dodecnyl, tetracenyl, hexadecenyl and octadecenyl. X is preferably -O-, -S- and -SO$_2$- and p is preferably 1.

If, within the scope of the preceding definition, $R^1$ to $R^8$ are $C_2$-$C_{18}$alkynyl-$(X)_p$, the alkynyl group can be linear or branched and can preferably contain 3 to 12, particularly 3 to 6, C atoms. The triple bond is preferably located in a terminal position. Some examples are ethynyl, propargyl, but-1-yn-3-yl, but-1-yn-4-yl, but-2-yn-1-yl, pent-1-yn-3- or -4- or -5-yl, hex-1-yn-3- or -4- or -5- or -6-yl, hex-2-yn-1- or -4- or -5- or -6-yl, hex-3-yn-1-yl, hex-3-yn-2-yl, heptynyl, octynyl, nonynyl, decynyl, undecynyl and dodecynyl. X is preferably -O-, -S- and -SO$_2$- and p is preferably 1.

If, within the scope of the preceding definitions, $R^1$ to $R^8$ are $C_3$-$C_8$cycloalkyl-$(X)_p$, the latter can be cyclopropyl, cyclobutyl, cyclopentyl, cyclohexyl, cycloheptyl or cyclooctyl. X is preferably -O-, -S-or -SO$_2$-. $C_3$-$C_6$-cycloalkyl is preferred and p is preferably 1.

If, within the scope of the preceding definitions, $R^1$ to $R^8$ are $C_3$-$C_8$cycloalkyl-$C_rH_{2r}$-$(X)_p$ or ($C_1$-$C_{12}$alkyl)-$C_3$-$C_8$cycloalkyl-$(X)_p$ or ($C_1$-$C_{12}$alkyl)-$C_3$-$C_8$cycloalkyl-$C_rH_{2r}$-$(X)_p$, the alkyl group can be linear or branched and can preferably contain 1 to 6, particularly 1 to 4, C atoms. R in the -$C_rH_{2r}$- group is preferably 1. X is preferably -O-, -S- or -SO$_2$-. The cycloalkyl group in these substituents is preferably $C_3$-$C_6$cycloalkyl and p is preferably 1.

If, within the scope of the preceding definitions, $R^1$ to $R^8$ are ($C_1$-$C_{12}$-alkyl)-phenyl-$X)_p$, phenyl-$C_rH_{2r}$-$X)_p$ or ($C_1$-$C_{12}$-alkyl)-phenyl-$X)_p$, the alkyl group can be linear or branched and can preferably contain 1 to 6, particularly 1 to 4, C atoms. r in the -$C_rH_{2r}$-group is preferably 1, X is preferably -O-, -S- or -SO$_2$-and p is preferably 1.

Within the scope of the preceding definitions, $R^1$ to $R^8$ can be unsubstituted or monosubstituted or polysubstituted, preferably monosubstituted to trisubstituted and particularly monosubstituted or disubstituted. If the substituent is halogen, this is preferably -F, -Cl or -Br. If the substituent is -CONR$^9$R$^{10}$, R$^9$ and R$^{10}$ independently of one another are preferably H or $C_1$-$C_4$alkyl, particularly methyl or ethyl. If the substituent is -OR$^9$, -SR$^9$ or -COOR$^9$, R$^9$ is preferably H, C$_1$-C$_4$alkyl or (C$_m$H$_{2m}$O)$_q$R$^{11}$ in which R$^{11}$ is H or C$_1$-C$_4$alkyl and m is 2 or 3 and q is 1 to 12.

If, within the scope of the preceding definitions, R$^1$ to R$^8$ are halogen, this is -F, -Cl or -Br, particularly -F and -Cl.

If, within the scope of the preceding definitions, R$^1$ to R$^8$ are -COOR$^9$ or -CONR$^9$R$^{10}$, R$^9$ and R$^{10}$ independently of one another are preferably C$_1$-C$_6$alkyl, or R$^9$ and R$^{10}$ together are preferably tetramethylene, pentamethylene or 3-oxapentylene.

If, within the scope of the preceding definitions, R$^1$ to R$^8$ are -Si(C$_1$-C$_4$alkyl)$_3$, this is preferably -Si(C$_1$alkyl or C$_2$alkyl) and particularly trimethylsilyl.

If, within the scope of the preceding definitions, R$^1$ to R$^8$ are -S(C$_m$H$_{2m}$-O)$_n$R$^{11}$ or -O(C$_m$H$_{2m}$-O)$_n$R$^{11}$, R$^{11}$ is preferably H or C$_1$-C$_4$alkyl, m is preferably 2 or 3 and n is preferably 1 to 12, particularly 1 to 6.

Adjacent radicals for the groups -CO-O-CO- and -CO-NR$^9$-CO- are particularly R$^2$ and R$^3$ and/or R$^6$ and R$^7$.

As alkyl, R$^9$ and R$^{10}$ preferably contain 1 to 6 C atoms, particularly 1 to 4 C atoms, and are especially methyl or ethyl. The alkyl can be linear or branched.

If R$^9$ and R$^{10}$ are the group (C$_m$H$_{2m}$-O)$_q$R$^{11}$, m is preferably 2 or 3, q is 1 to 12, particularly 2 to 6, and R$^{11}$ is H or C$_1$-C$_4$alkyl.

In a preferred embodiment R$^9$ and R$^{10}$ independently of one another are H, C$_1$-C$_4$alkyl or phenyl, or R$^9$ and R$^{10}$ together are tetramethylene, pentamethylene or 3-oxapentylene.

In a preferred embodiment p is 1, and in another preferred embodiment R$^1$, R$^4$, R$^5$ and R$^8$ are H.

In another preferred embodiment R$^6$ or R$^7$, or R$^6$ and R$^7$, are a substituent and R$^1$ to R$^5$ and R$^8$ are H. An embodiment in which R$^6$ or R$^6$ and R$^7$ and also R$^2$ or R$^2$ and R$^3$ are a substituent and R$^1$, R$^5$, R$^5$ and R$^8$ are H is also preferred.

A preferred embodiment of compounds of the formula I is constituted by those in which R$^1$ to R$^4$ are H and R$^5$ to R$^8$ are each H and at least one of the radicals R$^5$ to R$^8$ independently of one another is a substituent belonging to the group comprising C$_1$-C$_{18}$alkyl(X)$_p$, C$_3$-C$_{12}$alkenyl(X)$_p$, C$_3$-C$_{12}$alkynyl(X)$_p$, C$_5$cycloalkoxy-(X)$_p$, C$_6$cycloalkyl(X)$_p$, (C$_1$-C$_6$alkyl)-C$_5$cycloalkyl(X)$_p$, (C$_1$-C$_6$alkyl)-C$_6$cycloalkyl(X)$_p$, C$_5$cycloalkyl-CH$_2$(X)$_p$, C$_6$cycloalkyl-CH$_2$(X)$_p$, (C$_1$-C$_6$alkyl)-C$_5$cycloalkyl-CH$_2$(X)$_p$, (C$_1$-C$_6$alkyl)-C$_6$cycloalkyl-CH$_2$(X)$_p$, phenyl-(X)$_p$, (C$_1$-C$_6$alkyl)-phenyl(X)$_p$, benzyl(X)$_p$ or (C$_1$-C$_6$alkyl)-benzyl(X)$_p$ each of which is unsubstituted or substituted by -F, -Cl, -CN, -CONR$^9$R$^{10}$, -OR, -SR$^9$ or -COOR$^9$; X is -O-, -S-, -SO- or -SO$_2$- and p is 0 or 1; or R$^5$ to R$^8$ independently are a substituent belonging to the group comprising -CF$_3$, -CN, -Si(C$_1$alkyl or C$_2$alkyl)$_3$, -S(C$_m$H$_{2m}$-O)$_n$R$^{11}$ or -O(C$_m$H$_{2m}$-O)$_n$R$^{11}$; or one of each of R$^5$ to R$^8$ is -F or -Cl and at least one further member of R$^5$ to R$^8$ is a substituent of the groups defined above, including C$_1$-C$_4$alkyl and methoxy; R$^9$ and R$^{10}$ independently of one another are H, C$_1$-C$_6$alkyl or -CH$_2$CH$_2$OH, or R$^9$ and R$^{10}$ together are tetramethylene, pentamethylene or -CH$_2$CH$_2$NR$^9$CH$_2$CH$_2$- and R$^{11}$ is H or C$_1$-C$_4$alkyl; and m is 2 or 3 and n is a number from 2 to 12.

Compounds of the formula I which are particularly preferred are those in which R$^1$ to R$^5$ and R$^8$ are H and R$^6$ is a substituent and R$^7$ is H, or R$^6$ and R$^7$ are a substituent belonging to the group comprising -Si(CH$_3$)$_3$; -CF$_3$; -CN; C$_1$-C$_6$alkyl or benzyl, each of which is substituted by -COOR$^9$; C$_1$-C$_{18}$alkoxy or C$_1$-C$_{18}$alkylthio each of which is unsubstituted or substituted by -OH; phenyl-X-, benzyl-X-, C$_1$-C$_4$alkylphenyl-X- or C$_1$-C$_4$alkylbenzyl-X-, each of which is unsubstituted or substituted by -F, -Cl, -OH, C$_1$-C$_4$alkoxy or C$_1$-C$_4$alkylthio and in which X is -O-, -S- or -SO$_2$-; or unsubstituted C$_3$-C$_{12}$alkenyloxy.

Another preferred embodiment is constituted by compounds of the formula I in which R$^1$, R$^4$, R$^5$ and R$^8$ are H and at least one of R$^2$ and R$^3$ and also of R$^6$ and R$^7$ is a substituent belonging to the group comprising -COOR$^9$, -CONR$^9$R$^{10}$ or C$_1$-C$_{18}$alkyl(X)$_p$, C$_3$-C$_{12}$alkenyl(X)$_p$, C$_3$-C$_{12}$alkynyl(X)$_p$, C$_5$cycloalkyl(X)$_p$, C$_6$cycloalkyl(X)$_p$, (C$_1$-C$_6$alkyl)-C$_5$cycloalkyl(X)$_p$, (C$_1$-C$_6$alkyl)-C$_6$cycloalkyl(X)$_p$, C$_5$cycloalkyl-CH$_2$(X)$_p$, C$_6$cycloalkyl-CH$_2$(X)$_p$, (C$_1$-C$_6$alkyl)-C$_5$cycloalkyl-CH$_2$-(X)$_p$, (C$_1$-C$_6$alkyl)-C$_6$cycloalkyl-CH$_2$(X)$_p$, phenyl(X)$_p$, (C$_1$-C$_6$alkyl)-phenyl(X)$_p$, benzyl(X)$_p$ or (C$_1$-C$_6$alkyl)-benzyl(X)$_p$ each of which is unsubstituted or substituted by -F, -Cl, -CN, -CONR$^9$R$^{10}$, -OR$^9$, -SR$^9$ or -COOR$^9$; X is -O-, -S-, -SO- or -SO$_2$- and p is 0 or 1; or belonging to the group comprising -CF$_3$ -CN, -Si(C$_1$alkyl or C$_2$alkyl)$_3$, -S(C$_m$H$_{2m}$-O)$_n$R$^{11}$ or -O-C$_m$H$_{2m}$-O)$_p$R$^{11}$; or R$^2$ and R$^3$ together are -CO-O-CO- or -CO-NR$^9$-CO- and at least one of R$^6$ and R$^7$ is one of the substituents defined above, or R$^6$ and R$^7$ together are -CO-O-CO- or CO-NR$^9$-CO-; R$^9$ and R$^{10}$ independently of one another are H, C$_1$-C$_6$alkyl or -CH$_2$CH$_2$OH, or R$^9$ and R$^{10}$ together are tetramethylene, pentamethylene or -CH$_2$CH$_2$NR$^9$CH$_2$CH$_2$-; and m is 2 or 3 and n is a number from 2 to 12. Compounds of the formula I which are particularly preferred in this connection are those in which the substituent is selected from the group comprising -COOR$^9$; -Si(CH$_3$)$_3$; -CF$_3$; -CN; C$_1$-C$_6$alkyl or benzyl, each of which is substituted by -COOR$^9$; C$_1$-C$_{18}$alkoxy or C$_1$-C$_{18}$alkylthio, each of which is unsubstituted or substituted by -OH; phenyl-X-, benzyl-X-, C$_1$-C$_4$alkylphenyl-X- or C$_1$-C$_4$alkylbenzyl-X-, each of which is unsubstituted or substituted by -F, -Cl, -OH, C$_1$-C$_4$alkoxy or C$_1$-C$_4$alkylthio and in which X is -O-, -S- or -SO$_2$-; or unsubstituted C$_3$-C$_{12}$alkenyloxy. Substituents which are particularly selected in this connection are -CF$_3$, C$_1$-C$_{18}$alkoxy and -COOR$^9$.

The preparation of compounds of the formula I can be effected by known processes or by a novel process. Central intermediates in this connection are appropriately substituted naphthacene-5,12-diones of the formula III

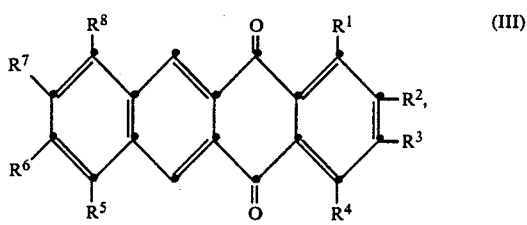

some of which are known or which can be prepared, for example, by the following processes.

The compounds of the formula III can be prepared by reacting a naphthalenedicarboxylic anhydride of the formula IV

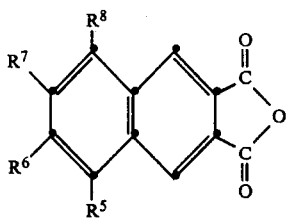

(IV)

in the presence of a Lewis acid with a benzene of the formula V

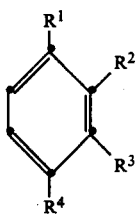

(V)

in which formulae $R^1$ to $R^8$ are as defined above, and, if appropriate, by substituting compounds of the formula III in which at least one of $R^1$ to $R^8$ is -$NO_2$ or halogen, by a nucleophilic compound. Halogen is preferably -Br, -Cl and, particularly, -F. Compounds suitable for the nucleophilic substitution are especially those of the formula ($R^1$ to $R^8$)-X-H in which X is -O-, -S-, -SO- or -$SO_2$-, malonic acid esters or nitriles and phenylacetonitrile. The compounds can be used in the form of their alkali metal salts, for example Li, Na or K salts. It is also possible to carry out the nucleophilic substitution in the presence of bases, for example alkali metal hydroxide or carbonate solutions.

The compounds of the formula III can also be prepared by reacting, in a Diels-Alder reaction, a compound of the formula VI

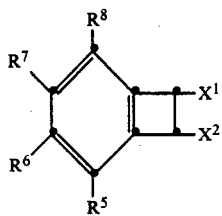

(VI)

in which $R^5$, $R^6$, $R^7$ and $R^8$ are as defined above and can, in addition, be -$NO_2$ and $X^1$ and $X^2$ independently of one another are -Cl, -Br or -I, with the elimination of $HX^1$ and $HX^2$, with a compound of the formula VII

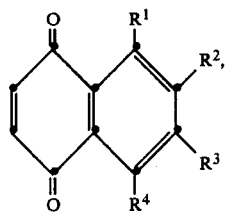

(VII)

in which $R^1$, $R^2$, $R^3$ and $R^4$ are as defined above and can, in addition, be -$NO_2$. In the substituents $R^1$ to $R^8$ p is preferably 1.

This reaction is advantageously carried out at temperatures from 50° to 250° C., preferably 80° to 200° C. It is advantageous to use an inert solvent, for example polar, aprotic solvents. Some examples are aromatic hydrocarbons (benzene, toluene, xylene, chlorobenzene and dichlorobenzene), nitriles (acetonitrile), ethers (dibutyl ether, dioxane, tetrahydrofuran, ethylene glycol dimethyl ether or diethylene glycol dimethyl ether). Isolation and purification can be effected by customary methods, for example crystallization, sublimation or chromatography.

Some of the compounds of the formula VI are known (see, for example, H. P. Cava et al., J. Am. Chem. Soc. page 1701 (1957) and J. W. Barton et al., J. Chem. Soc. Perkin Trans. 1, pages 967–971 (1986)), or can be prepared by analogous processes. Some of the substituted 1,2-bis(dichloromethyl or dibromomethyl)-benzenes required for the preparation are also in part known or can be obtained by customary electrophilic or nucleophilic substitution reactions of corresponding o-dimethylbenzenes, followed by chlorination or bromination with, for example, N-chloro-succinimide or N-bromosuccinimide.

The 1,4-naphthoquinones of the formula VII are known and can be obtained, for example, by nucleophilic substitution of appropriately protected and substituted halogeno-1,4-naphthoquinones or nitro-1,4-naphthoquinones with, for example, the compounds described above in the presence of alkali metal compounds ($K_2CO_3$, $Cs_2CO_3$, KOH, NaOH, $NaNH_2$, $NaOCH_3$ or $NaOC_2H_5$) or by means of alkali metal compounds, for example those of Li, K, Na, Rb or Cs. Halogenonaphthoquinones and nitronaphthoquinones are described, for example, in Houben-Weyl, Quinones I, volume 7/3b (1977). The naphthoquinones of the formula VII can also be prepared in a known manner by electrophilic or nucleophilic substitution of appropriately substituted naphthalenes, dihydronaphthalenes or tetrahydronaphthalenes and subsequent conversion of the products into the substituted 1,4-naphthoquinones.

The compounds of the formula III can also be prepared by reacting 1,2-bis-(dihalogenomethyl)-benzenes of the formula

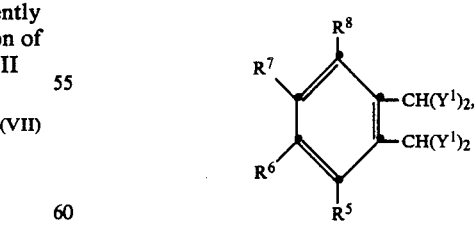

in which $Y^1$ is Cl, Br or I, with a compound of the formula VII in the presence of NaI in an organic solvent. This method has been described by J. W. McOmie in Synthesis, pages 416–417 (1973).

Compounds of the formula I can also be obtained by reacting anthracene-1,4-quinones of the formula

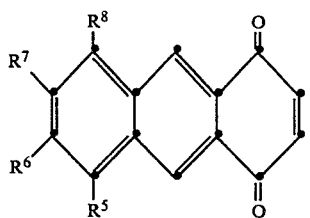

with an α-pyrone of the formula VIII

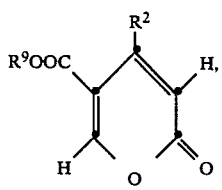

or with a butadiene of the formula IX

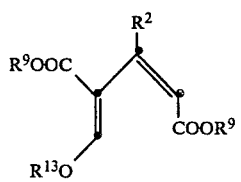

in which $R^{13}$ is $C_1$–$C_6$alkyl and $R^9$ is as defined above and is preferably $C_1$–$C_6$alkyl. This method and the preparation of α-pyrones is described in U.S. Pat. No. 4,617,151 and EP-A No. 0,195,743.

Compounds of the formula VIII and IX can be obtained, for example, in the following manner, $X^1$ being an alkali metal:

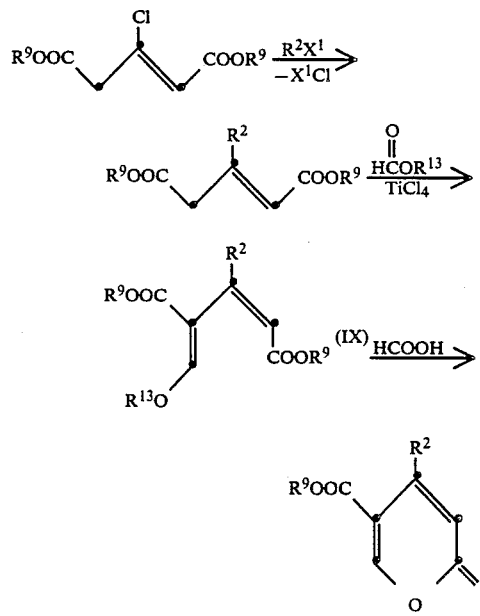

If $R^1$ to $R^8$ are a polyoxoalkylene radical, compounds of this type are also obtained by reacting compounds of the formula I in which $R^1$ to $R^8$ are hydroxyalkoxy with epoxides. It is also possible to modify the radicals $R^1$ to $R^8$ by classical reactions, for example hydrolysis, esterification, transesterification, amidation, oxidation, reduction or dehydrogenation. Carboxylic acid esters can be converted into the trifluoromethyl derivatives in a known manner by means of $HF/SF_4$.

The compounds of the formula I can be obtained by various reaction routes from the naphthacene diones of the formula III.

In a novel process 5,12-diacyloxynaphthacenes of the formula X

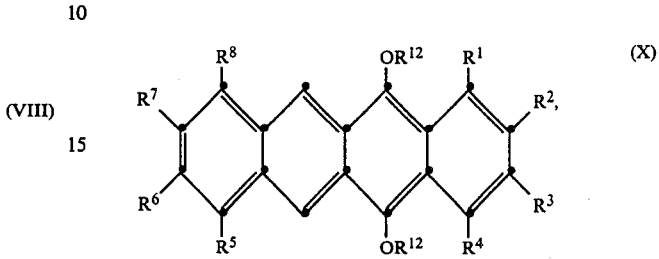

in which $R^1$ to $R^8$ independently of one another are, for example, H and at least one of $R^1$ to $R^8$ is a substituent belonging to the group comprising -F, -Si($C_1$–$C_4$alkyl)$_3$ or -COOR$^{10}$; or each pair of adjacent radicals of $R^1$ to $R^8$ is -CO-O-CO-; or at least one of $R^1$ to $R^8$ is $C_1$–$C_{20}$alkyl-(X)$_{\overline{p}}$, $C_3$–$C_8$cycloalkyl-(X)$_{\overline{p}}$, $C_1$–$C_{12}$alkyl-$C_3$–$C_8$cycloalkyl-(X)$_{\overline{p}}$, $C_3$–$C_8$cycloalkyl-$CH_2$-(X)$_{\overline{p}}$, $C_1$–$C_{12}$alkyl-$C_3$–$C_8$cycloalkyl-$CH_2$-(X)$_{\overline{p}}$, $C_6$–$C_{10}$aryl-X-, $C_7$–$C_{20}$alkaryl-X-, $C_7$–$C_{12}$aralkyl-(X)$_{\overline{p}}$ or $C_8$–$C_{20}$alkaralkyl-(X)$_{\overline{p}}$ or -Y-($C_mH_{2m}$-O)$_{\overline{n}}$R$^{10}$ each of which is unsubstituted or substituted by -F, -OH, $C_1$–$C_{12}$alkoxy, $C_1$–$C_{12}$acyloxy or -COOR$^{10}$; R$^{10}$ is H or $C_1$–$C_{18}$alkyl, X is -O-, -S-, -SO- or -$SO_2$-and Y is -O- or -S- and p is 0 or 1, m is a number from 2 to 6 and n is a number from 2 to 20; and $R_{12}$ is $C_1$–$C_4$acyl which is unsubstituted or substituted by -F, especially acetyl, are obtained by reductive acylation from the naphthacene diones of the formula III in a manner known per se [compare T. Kametani in Chem. Pharm. Bull. 26(12), pages 3820–3825 (1978)].

The compounds of the formula X can be converted into the corresponding compounds of the formula I by direct reaction with sulfur in a solvent, for example 1,2,4-trichlorobenzene, and in the presence of catalytic amounts of a sulfonic acid, for example p-toluenesulfonic acid, at temperatures between 100° and 300° C.

The naphthacene diones of the formula III can be reduced in a manner known per se [see Ch. Marschalk, Bull. Soc. Chim. France 427 (1948) and pages 931 and 1122 (1939 and also EP-A No. 0,153,905] to give a correspondingly substituted 5,12-dihydrotetracene or tetracene and these can be converted directly by means of sulfur into the corresponding tetrathiotetracenes.

The tetracenes can be chlorinated in a known manner (see EP-A No. 0,153,905) to give compounds of the formula II

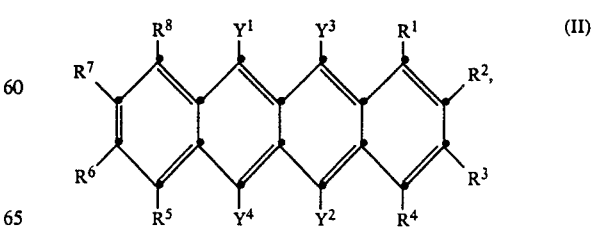

in which $R^1$ to $R^8$ are as defined above, $Y^1$ and $Y^2$ are -Cl and $Y^3$ and $Y^4$ are H, or $Y^3$ and $Y^4$ are -Cl and $Y^1$ and Y² are H. The compounds of the formula II can be reacted in a known manner with sulfur, selenium or an alkali metal sulfide or selenide in a general process for the preparation of the compounds of the formula I.

In all the intermediate stages it is possible to modify the radicals R¹ to R⁸ by classical reactions mentioned above.

The compounds of the formula I are predominantly crystalline and coloured compounds, the properties of which can be influenced in a controlled manner by the degree of substitution and the nature of the substituents: for example the oxidation potential; or the position of the absorption maximum, which can be shifted into the longer-wave region, which is advantageous for laser-optical applications.

Electrically conductive charge-transfer complexes (CT complexes) can be prepared from the compounds of the formula I by means of electron acceptors. They can be attached to polymers by means of their functional substituents, for example they can be incorporated into polymers as side groups (cf. U.S. Pat. No. 4,617,151). The CT complexes are also suitable for the preparation of, for example, antistatic coatings of photographic film elements, magnetic tapes, electrophotographic film elements and electronic components (see U.S. Pat. No. 3,634,336). The chalcogenated tetracenes also display electrochromic properties; they can be used for electrochromic displays. By virtue of their long-wave $\lambda_{max}$, some are also suitable for use as laser-optical data storage units [Nach. Chem. Techn. Lab. 35, pages 255 et seq. (1987)]. They can also be employed as anode material in organic solid state batteries (EP-A No. 0,090,598). CT complexes of substituted tetrathiotetracenes or tetraselenotetracenes can also be incorporated into thermoplastic, thermosetting or elastomeric polymers in order to achieve antistatic properties. For this purpose it is advantageous to dissolve, for example, the substituted tetrathiotetracenes or tetraselenotetracenes, together with a soluble polymer or a precursor thereof and an electron acceptor, for example an agent which forms halogen (organic halogenated compounds, for example bromoform, trichlorobromomethane, tetrabromomethane, hexachloropropane, perchlorobutadiene, 1,3-dichloro-2-butene, 1,4-dichloro-2-butene, 1,4-bis-(trichloromethyl)-benzene, iodoacetonitrile, iodoform, tetrachloroethylene, perchlorocyclobutadiene, N-chlorosuccinimide, N-bromosuccinimide or N-iodosuccinimide), if appropriate together with another inert solvent, and to remove by evaporation at an elevated temperature the excess agent which forms halogen and the solvent. The resulting composition contains a network of needle-shaped crystals of the CT complex in the polymer, if the chalcogenated tetracene is unsubstituted or contains small substituents (for example F, CH₃ or CF₃). Compositions of this type exhibit a high electrical conductivity. This can be improved further if a substituted tetrathiotetracene or tetraselenotetracene of the formula I which does not form such a network and which is present in the polymer matrix in a state of fine distribution is concomitantly used, since substituted tetrathiotetracenes or tetraselenotetracenes of this type have no tendency, or only a slight tendency, to crystallize in the polymer.

The following examples illustrate the invention in greater detail.

(A) Preparation of starting materials

Examples a–g: 31.05 mmol of zinc powder are added, with stirring, to 10.35 mmol of 2-substituted naphthacene-5,12-dione, 40 ml of ethyl acetate, 25 ml of acetic anhydride and 31.05 mmol of potassium acetate. After being stirred for 40 minutes at 25° C., the reaction mixture is filtered and the residue is washed four times with CH₂Cl₂. The filtrates are evaporated, and the residue is recrystallized from CH₂Cl₂/pentane and then from toluene. The yields and melting points of the resulting 2-substituted 5,12-diacetoxynaphthacenes are shown in Table 1.

TABLE 1

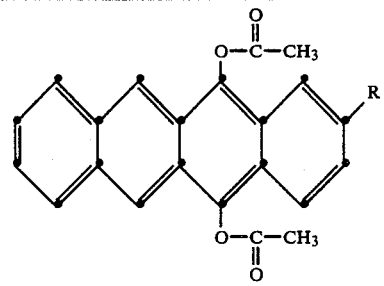

| Example No. | R | Yield (%) | Melting Point (°C.) |
|---|---|---|---|
| a | —OCH₂CH₃ | 79 | 150–153 |
| b | —OCH₂—CH(C₂H₅)(CH₂)₃CH₃ | 71 | 130–135 |
| c | —O-n-C₈H₁₇ | 84 | 107–111 |
| d | —O-n-C₁₈H₃₇ | 49 | 155–157 |
| e | —SCH₂CH₃ | 77 | 130–135 |
| f | —C(CH₃)(COOC₂H₅)₂ | 63 | 230 (decomposition) |
| g | —CF₃ | 91 | >250 |

The corresponding 2-substituted naphthacene-5,12-diones of Examples a–f can be obtained by nucleophilic substitution of 2-fluoronaphthacene-dione.

Example h: 2-(Trifluoromethyl)-naphthacene-dione 5.65 g (25 mmol) of 6-(trifluoromethyl)-1,4-naphthoquinone, 9.82 g (approx. 37 mmol) of 1,2-dibromobenzocyclobutene (containing a little 2-bromo-1-iodobenzocyclobutene as an impurity) and 100 ml of xylene are kept under reflux for 16 hours under a water separator. The mixture is cooled and the precipitate is filtered off and washed with xylene. Yield 5.82 g (71%); melting point 253°–254° C.

An analogous procedure is used in the preparation of the 2,3-bis-(trifluoromethyl)-naphthacene-5,12-dione used in Example i below (yield 59%; melting point >280° C.).

Example i: 1.65 mmol of 2,3-bis-(trifluoromethyl)-naphthacene-5,12-dione, 5 ml of ethyl acetate, 4.96 mmol of potassium acetate and 3 ml of acetic anhydride are hydrogenated for 35 minutes at 20°–25° C., with the addition of 0.1 g of Pd/C (5%). The mixture is filtered and the residue is extracted by washing three times with CH₂Cl₂. The filtrates are evaporated and the residue is recrystallized from CH₂Cl₂/pentane. Yield 76% of 2,3-bis-(trifluoromethyl)-5,12-diacetoxynaphthacene; melting point >250°.

Examples j–m: 2-(2'-Hydroxyethoxy)-naphthacene-5,12-dione 27.6 g (0.1 mol) of 2-fluoro-5,12-naphthacenedione, 32.5 g (0.1 mol) of Cs₂CO₃ and 300 ml of ethylene glycol are initially placed in a sulfonation flask under nitrogen. After being heated to 125° C. the mixture is stirred for three and a quarter hours. The reaction mixture is then poured into 3000 ml of water containing hydrochloric acid, and the precipitated product is filtered off and washed several times with water. After being dried in vacuo at 80° C. 30.3 g (97.1%) of pure product are obtained, melting point 208.8° C. An analogous procedure is used in Examples k–m (see Table 2).

Example n: 2-(3'-Butenoxy)-naphthacene-5,2-dione 10 g (0.036 mol) of 2-fluoro-5,12-naphthacenedione, 26 g (0.028 mol) of $Cs_2CO_3$ and 10.41 g (0.14 mol) of 3-butenol are initially placed under nitrogen in 200 ml of DMF. The reaction mixture is heated to 125° C. and is stirred for four and a half hours. After precipitation in 4000 ml of water containing hydrochloric acid, the product is filtered off (crude yield 94%). 64% of pure product are obtained after chromatography over silica gel ($CH_2Cl_2$); melting point 149° C.

TABLE 2

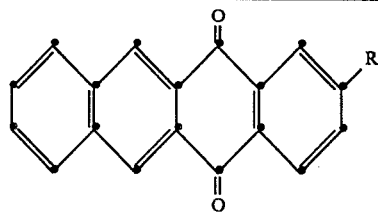

| Example | R | m.p. (°C.) | Reaction time (hours) | Yield (%) | Solvent | Reaction time (°C.) |
|---|---|---|---|---|---|---|
| j | O—$(CH_2)_2$—OH | 208 | 3¼ | 97 | i.S. | 125 |
| k | O—$(CH_2)_4$—OH | 190 | 7½ | 70 | i.S. | 120 |
| l | O—$(CH_2)_6$—OH | 153 | 1¼ | 70 | DMSO | 120 |
| m | O—$(CH_2)_{10}$—OH | 113 | ¾ | 73 | i.S. | 125 |
| n | O—$(CH_2)_2$—CH=$CH_2$ | 149 | 4¼ | 63 | DMF | 125 | i.S.: The alcohol is also the solvent
DMF: Dimethylformamide

Example o: 2-Cyanonaphthacene-5,12-dione 10 g (33.2 mmol) of naphthacene-5,12-dione-2-carboxamide, 10.18 g (66.4 mmol) of $POCl_3$ and 200 ml of DMF are stirred for 2 hours at 10° C. and then for 2 hours at 25° C. The mixture is discharged into ice water. The precipitate is filtered off, washed three times with water and dried. After recrystallization from o-dichlorobenzene, 7.35 g (78%) of crude product are obtained.

IR Spectrum (KBr): 1678 $cm^{-1}$: quinone: 2240 $cm^{-1}$: CN

Mass spectrum: M/e=283 (M+) (base peak); 255; 227; 226; 100.

Example p: A mixture of 0.1 mol of 4-trimethylsilyl-1,2-bisdibromomethylbenzene, 0.12–0.2 mol of substituted naphthoquinone, 0.6 mol of sodium iodide and 1000 ml of acetone or acetonitrile is boiled under reflux for 5 hours with stirring and under an $N_2$ atomosphere. After cooling, the precipitate which has been deposited is filtered off and digested with water. The filtrate obtained in this way is evaporated to dryness and the residue is dissolved in $CH_2Cl_2$, washed with $NaHSO_3$ and dried. The residue is then subjected to steam distillation and the non-volatile fractions are extracted with ether, dried and then sublimed. 8-Trimethylsilylnaphthacene-5,12-dione of melting point 168°–170° C. is obtained in a 79% yield. 2,3-Trifluoromethyl-8-methoxynaphthacene-5,12-dione is obtained in a 33% yield in an analogous manner by direct sublimation of the filtrate, melting point >280° C.

Example q: The procedure is as in Example p, using acetone and appropriately substituted bis dibromomethylbenzenes and naphthoquinones, and subliming the filtrate directly. A 1:1 mixture of methyl 8-methoxynaphthacene-5,12-dione-2-carboxylate and 9-methoxynaphthacene-5,12-dione-2-carboxylate is obtained in a 50% yield, melting point 246°–248° C.

Example r: The naphthacene-5,12-diones of Examples j–p are reduced to the corresponding tetracenes by the following methods.

Method A 30 mmol of pyridine are dissolved in 25 ml of glacial acetic acid and stirred under reflux. 10 mmol of 2-R-naphthacene-5,12-dione and 60 mmol of zinc dust are mixed separately and the mixture is introduced into the above solution slowly, with stirring. After being stirred for 15 minutes under reflux, the mixture is discharged into hydrochloric acid/water, the bulk of the zinc is decanted off and the precipitate is filtered off. The residue is washed three times with water, dried and recrystallized from o-dichlorobenzene with filtration under hot conditions.

Method B 1.53 mol of aluminium turnings are initially placed in 1000 ml of butanol in a sulfonation flask equipped with a gas inlet, a reflux condenser and a stirrer. The reaction mixture is heated to reflux temperature. A strongly exothermic reaction sets in after an induction period of 5 to 15 minutes. The heating is removed and is replaced by an ice/water bath. The internal temperature should not exceed 100° C. The reaction is substantially complete after approx. 10 minutes. The solution is kept at reflux temperature for a further 30 minutes and is then filtered into another reaction vessel. 0.06 mol of 5,12-naphthacenedione are then added and the mixture is heated under reflux for 12 hours, under nitrogen and with stirring. The reaction mixture is then poured into 3000 ml of 15% HCl and the resulting mixture is homogenized with ethanol. The precipitated product is filtered off, washed with methanol and water and dried in vacuo at 70° C. Further purification is carried out by recrystallization from chlorobenzene.

TABLE 3

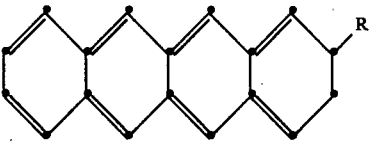

| R² | Method | Yield (%) | m.p. (°C.) |
|---|---|---|---|
| —CN | A | 32 | >250 |
| —O(CH₂)₂—OH | B | 73 | 316 |
| —O(CH₂)₄—OH | B | 70 | 293 |
| —O(CH₂)₆—OH | B | 46 | 271 |
| —O(CH₂)₁₀—OH | B | 60 | 254 |
| —O(CH₂)₂—CH=CH₂ | B | 69 | 275 |
| —Si(CH₃)₃ | A | 13 | >260 |

Example s: Reduction to dihydrotetracenes

A mixture of 0.08 mol of appropriately substituted naphthacene-5,12-dione, 0.24 mol of pyridine, 0.48 mol of zinc and 600 ml of glacial acetic acid is boiled under reflux for 4 hours under an N₂ atmosphere and with stirring. A further 0.24 mol of zinc is then added and the mixture is boiled under reflux for 16 hours. The reaction solution is then filtered while hot and the filtrate is evaporated to dryness in vacuo. The residue is partitioned between CH₂Cl₂ and water, and the organic phase is washed with NaHCO₃ solution and 1N HCl. After the solvent has been removed by evaporation, the residue is flash-chromatographed using CH₂Cl₂ (cf. Table 4).

TABLE 4

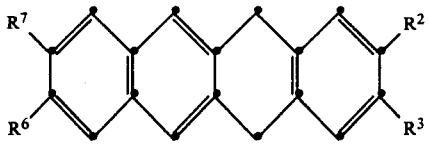

| R² | R³ | R⁶ | R⁷ | Yield (%) | m.p. (°C.) |
|---|---|---|---|---|---|
| —COOCH₃ | H | —OCH₃ᵃ | H | 57 | 162–165 |
| —CF₃ | —CF₃ | —OCH₃ | H | 66 | oil |
| —CF₃ | —CF₃ | —COOCH₃ | COOCH₃ | 30 | 186–188 |

ᵃ1:1 Mixture of the 8- and 9-position isomers

Example t: Dehydration to tetracene

A mixture of 4 mmol of substituted dihydronaphthacene, 4 mmol of chloranil and 70 ml of glacial acetic acid is heated under reflux for 1–4 hours under an N₂ atmosphere and with stirring. After cooling, the crystals formed are removed and washed with CH₂Cl₂ and methanol (see Table 5a).

TABLE 5a

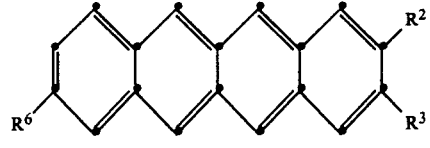

| R² | R³ | R⁶ | Yield (%) | m.p. (°C.) |
|---|---|---|---|---|
| —COOCH₃ | H | —OCH₃ᵃ | 95 | >280 |
| —CF₃ | —CF₃ | —OCH₃ | 27 | 167–168 |

The tetracenes listed in table 5b are prepared analogously.

TABLE 5b

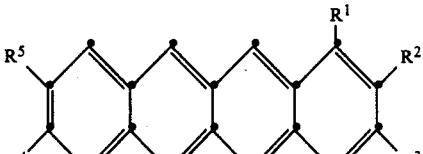

| R¹ | R² | R³ | R⁴ | R⁵ | λ$_{max}$ (nm) |
|---|---|---|---|---|---|
| | —CO—O—CO | | —OCH₃ | | 446 |
| | —COOC₂H₅ | —COOC₂H₅ | —OCH₃ | | 496 |
| | —CONH₂ | | —OCH₃ | | 493 |
| —CF₃ | —COOCH₃ | | | —OCH₃ | 512 |
| —CF₃ | —COOCH₃ | | —OCH₃ | | 503 |
| | —CF₃ | —CF₃ | —CF₃ | —CF₃ | 467 |
| | —CF₃ | —CF₃ | —CF₃ | | 472 |
| | —CN | | —OCH₃ | | 503 |
| | —CONH₂ | | —OCH₃ | | 493 |

Example u: 2,3-Dicyanotetracene

A mixture of 3.5 g of anthracene-2,3-dialdehyde (E. Mallonli et al., Synthesis 1980, page 689), 1.8 g of succinodinitrile, 3 g of K₂CO₃ and 250 ml of dimethyl sulfoxide is heated with stirring at 60°–70° C. for 30 minutes. It is then cooled to 15° C. and 50 ml of water are added. The precipitate which has been deposited is filtered off and is sublimed at 300° C. Yield 485 mg (12%), λ$_{max}$: 772 nm.

(B) Preparation Examples

Examples 1–6: 1.83 mmol of substituted naphthacene-5,12-diacetate, 15.8 milliequivalents of S₈ and 0.026 mmol of p-toluenesulfonic acid in 100 ml of 1,2,4-trichlorobenzene are heated under reflux for five and a half hours under a gentle stream of argon in a 250 ml flask equipped with a reflux condenser and a gas inlet tube. The dark green solution is then evaporated under a high vacuum.

The crude product is chromatographed using CCl₄ over a silica gel flash column (240 g of silica gel 518 7 cm). [The silica gel must previously be treated with CCl₄ containing 2% of triethylamine and then be washed with pure CCl₄ until the eluate is once more neutral.] The fractions having a dark green colour contain the purified 2-substituted 5,6,11,12-tetrathiotetracene. Spectral data and yields are given in Table 6.

TABLE 6

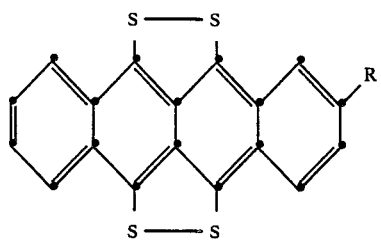

| Example No. | R | Mass spectrum (M+) | λmax (nm) in 1,2,4-tri-chlorobenzene | Yield (%) |
|---|---|---|---|---|
| 1 | —OC$_2$H$_5$ | 396 | 700 | 24[a] |
| 2 | —O-n-C$_8$H$_{17}$ | 480 | 699 | 50[b] |
| 3 | —OCH$_2$CH(C$_2$H$_5$)(CH$_2$)$_3$CH$_3$ | 480 | 698 | 8[a] |
| 4 | —O-n-C$_{18}$H$_{37}$ | 620 | 698 | 50[a] |
| 5 | —C(CH$_3$)(COOC$_2$H$_5$)$_2$ | 524 | 704 | 10[a] |
| 6 | —SC$_2$H$_5$ | 412 | 711 | 3% |

[a] sublimed
[b] chromatographed

Example 7: 251 mg (0.61 mmol) of 2-trifluoromethyl-naphthacene-5,12-diacetate, 78 mg (2.43 milliequivalents) of S$_8$ and 2 mg (0.01 mmol) of p-toluenesulfonic acid in 35 ml of 1,2,4-trichlorobenzene are heated under reflux for 20 hours under a gentle stream of argon in a 100 ml small flask equipped with a reflux condenser and a gas inlet tube. After cooling, the solvent is removed by evaporation under high vaccum (HV), the residue is extracted by boiling with hexane, and the black powder is filtered off and dried at 60° C. under HV. This gives 203 mg (79%) of crude product.

This powder is sublimed at 190° C. (1.3×10$^{-4}$ mbar), 67.5 mg (35.6%) of pure 2-trifluoromethyl-5,6,11,12-tetrathiotetracene being obtained (small black needles).

Mass spectrum: M$^+$=420.

λ$_{max}$ (1,2,4-trichlorobenzene): 725, 665 and 484 nm.

Example 8: 2,3-Trifluoromethyl-5,6,11,12tetrathiotetracene

The procedure of Example 7 is followed, using 2,3-trifluoromethylnaphthacene-5,12-diacetate. Yield: 75.6 mg (30%) after sublimation.

Mass spectrum: M$^+$=488.

λ$_{max}$ (1,2,4-Trichlorobenzene): 755 nm.

Example 9: 60 mg (0.2 mmol) of 2-trimethylsilyltetracene and 40 mg (12.5 mmol) of sulfur in 30 ml of 1,2,4-trichlorobenzene are refluxed for 18 hours under a gentle stream of argon in a 50 ml small flask equipped with a reflux condenser and a gas inlet tube. After the solution, which is now deep green, has been cooled, it is evaporated to dryness. The black crystalline solid is washed with 4×20 ml of hexane. Yield of 2-trimethylsilyl-5,6,11,12-tetrathiotetracene: 72 mg (85%).

Mass spectrum: M$^+$=424. The fragmentation is in accord with the expected structure.

λ$_{max}$ (trichlorobenzene): 712, 653 and 478 nm.

Examples 10 and 11: The procedure of Example 9 is followed, using appropriately substituted tetracenes (see Table 7a).

TABLE 7a

| Example | R$^2$ | R$^3$ | R$^6$ | Yield | λ$_{max}$ (trichlorobenzene) |
|---|---|---|---|---|---|
| 10 | —COOCH$_3$ | H | —OCH$_3$[a] | 85% (crude) | 738/743 |
| 11 | —CF$_3$ | —CF$_3$ | —OCH$_3$ | | 753 |

The tetrathiotetracenes of Table 7b are prepared analogously to Example 9.

TABLE 7b

| R$^1$ | R$^2$ | R$^3$ | R$^4$ | R$^5$ | λ$_{max}$ (nm) |
|---|---|---|---|---|---|
| —CF$_3$ | | —COOCH$_3$ | | —OCH$_3$ | 772 |
| —CF$_3$ | | —COOCH$_3$ | —OCH$_3$ | | 775 |
| | —CN | —CN | | | 805 |
| | —CF$_3$ | —CF$_3$ | —CF$_3$ | —CF$_3$ | 768 |
| | —COOCH$_3$ | —COOCH$_3$ | —CF$_3$ | —CF$_3$ | 768 |
| | —CF$_3$ | —CF$_3$ | —CF$_3$ | | 754 |
| | —CO—O—CO— | | —OCH$_3$ | | 776 |
| | —COOC$_2$H$_5$ | —COOC$_2$H$_5$ | —OCH$_3$ | | 763 |
| | —CN | | —OCH$_3$ | | 750 |
| | —CONH$_2$ | | —OCH$_3$ | | 738 |

Examples 12-17: 3.16 mmol of 2-R-naphthacene, 37 mmol of S$_8$ and 30 mg (92 E-6 mol) of caesium carbonate are initially placed in 30 ml of dimethyl sulfoxide (DMSO) under argon. The mixture is then heated to 120° C. and stirred for five and a half hours. The solution is introduced into water, and the mixture is filtered. The product is isolated after recrystallization from chlorobenzene (see Table 8).

TABLE 8

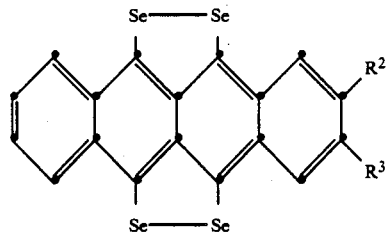

| Example | R² | Yield (%) | λ_max (nm) |
|---------|----|-----------| ---------- |
| 12 | —O(CH₂)₂OH | 45 | 696$^b$ |
| 13 | —O(CH₂)₄OH | 65 | 691$^b$ |
| 14 | —O(CH₂)₆OH | 58 | 697$^b$ |
| 15 | —O(CH₂)₁₀OH | 64 | 696$^b$ |
| 16 | —O(CH₂)₂—CH=CH₂ | 65 | 689$^c$ |
| 17 | —OCH₂C(CH₂OH)₂ CH₂—CH₃ | 73 | 694$^b$ |

$^b$DMSO
$^c$dimethylformamide (DMF)

Example 18: 1 mmol of 2-cyanotetracene in 20 ml of nitrobenzene (Fluka purest grade, dried over A4 molecular sieve) is initially placed under a gentle stream of argon in a 50 ml three-necked flask equipped with a gas inlet tube and a reflux condenser, and the mixture is cooled to 5° C. 297 mg (2.2 mmol) of sulfuryl chloride (Fluka purest grade) in 5 ml of nitrobenzene are added dropwise at such a rate that the temperature does not exceed 7° C. The mixture is then stirred for 1 hour at 5° C., in the course of which a beige precipitate is formed. The mixture is then allowed to warm up to room temperature and is then kept at 90° C. for 2 hours. After being cooled to room temperature, the reaction mixture is evaporated under a high vacuum, and the rust-brown solid is sublimed in a temperature gradient at an oven temperature of 170° C. Yield 134 mg (42% of small red needles). Melting point 225°-230°; mass spectrum: M⁺ =321 (2 Cl). 0.081 mmol of 2-cyanodichlorotetracene and 0.0324 mmol of Se₈ in 5 ml of Dowtherm A are heated at reflux temperature for 25 hours in a small 25 ml three-necked flask equipped with a gas inlet tube and a reflux condenser. In the course of this the reaction solution assumes an intense dark green colour. After cooling to room temperature, it is filtered and the dried black solid is sublimed at 280° C. under a high vacuum (10⁻⁷ mm Hg).

Yield 5 mg (~11%) of small black needles.

λ_max (1,2,3-Trichlorobenzene): 765, 700 and 493 nm. Mass spectrum: M⁺ =566 (4Se). The fragmentation is in accord with the expected structure of 2-cyano-5,6,11,12-tetraselenotetracehe.

Examples 19 and 21: The procedure followed is analogous to that of Example 18, using 2,3-dicyanotetracene, 2-trifluoromethyltetracene and 2,3-di-(trifluoromethyl)-tetracene (see Table 9).

TABLE 9

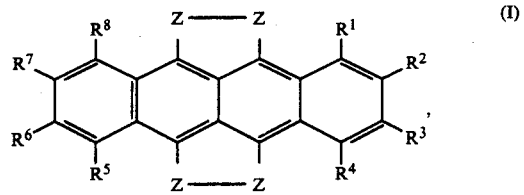

| Example | R² | R³ | Yield (sublimed, %) | λ_max (trichlorobenzene) |
|---------|-----|-----|----|-----|
| 19 | —CF₃ | H | 8,5 | 735 |
| 20 | —CF₃ | —CF₃ | 5 | 760 |
| 21 | —CN | —CN | 57 | 820 |

(C) Use Example: Electrochromism 1 mg of 2,3-di-(trifluoromethyl)-5,6,11,12-tetrathiotetracene and 100 mg of LiClO₄, dissolved in 5 ml of acetone, are added to the anode side of an electrochromic cell consisting of a Teflon membrane and an anode and cathode of ITO-glass at a mutual distance of 0.5 mm, and a solution of 1 mg of 2,3-di-(trifluoromethyl)-5,6,11,12-tetrathiotetracene perchlorate (CT complex) and 100 mg of LiClO₄ in 5 ml of acetone is added to the cathode side. After a voltage of 2 volts has been applied, the colour on the anode side changes within a few seconds from green to red-violet and the colour on the cathode side changes from red-violet to green. The original colours are obtained in both halves of the cell by reversing the polarity of the voltage. The same effect is observed if nitrobenzene or dimethylformamide is used as the solvent.

What is claimed is:

1. A compound of the formula (I)

[structure showing tetracene with substituents R¹-R⁸ and Z-Z bridges]

in which Z is -S- or Se- and
(a) R¹, R², R³ and R⁴ and H are at least one of the radicals R⁵ to R⁸ independently of one another is a substituent as defined hereinafter, and the other radicals R⁵ to R⁸ are H, said substituent being selected from the group of a1 to a3:
(a1) C₁–C₂₀alkyl-X)$_p$ with the exception of C₁–C₄alkyl and methoxy, the alkyl moiety being unsubstituted or substituted by halogen, -CN, -CONR⁹R¹⁰, -OR⁹, -SR⁹ or -COOR⁹,
(a2) C₂–C₁₈alkenyl(X)$_p$, C₂–C₁₈alkynyl(X)$_p$, C₃–C₈cycloalkyl(X)$_p$, (C₁–C₁₂alkyl)-C₃–C₈cycloalkyl(X)$_p$, C₃–C₈cycloalkyl-C$_r$H$_{2r}$(X)$_p$, (C₁–C₁₂alkyl)-C₃–C₈-cycloalkyl-C$_r$H$_{2r}$(X)$_p$, phenyl(X)$_p$, (C₁–C₁₂alkyl)phenyl(X)$_p$, phenyl-C$_r$H$_{2r}$(X)$_p$ and (C₁–C₁₂alkyl)phenyl-C$_r$H$_{2r}$(X)$_p$, each being unsubstituted or substituted by halogen, -CN, -CONR⁹R¹⁰, -OR⁹, -SR⁹ or -COOR⁹,
(a3) -Br, -CF₃, -CN, -Si(C₁-C₄alkyl)₃, -S-(C$_m$H$_{2m}$O)$_n$R¹¹ or -O(C$_m$H$_{2m}$-O)$_n$R¹¹, wherein X is -O-, -S-, -SO- or $SO_2$-, r is 1 or 2, p is 0 or 1, $R^9$ and $R^{10}$ independently of one another are H, $C_1$-$C_{12}$alkyl, phenyl or $(C_mH_{2m}\text{-}O)_{\overline{q}}R^{11}$, or $R^9$ and $R^{10}$ together are tetramethylene, pentamethylene, 3-oxapentylene or -$CH_2CH_2NR^9CH_2CH_2$-, $R^{11}$ is H or $C_1$-$C_{12}$alkyl, m is a number from 2 to 4, n is a number from 2 to 20 and q is a number from 1 to 20, or (b) $R^1$, $R^2$, $R^3$ and $R^4$ are H, at least one of $R^5$ to $R^8$ is -F or -Cl, at least one further member of $R^5$ to $R^8$ is a substituent selected from groups a1, a3, including $C_1$-$C_4$alkyl and methoxy, and the other members of $R^5$ to $R^8$ are H, or (c) at least one of $R^1$ to $R^4$ and at least one of $R^5$ to $R^8$ independently are a substituent selected from the groups -$COOR^9$, $CONR^9R^{10}$ and a1, a2 a3 defined above, including $C_1$-$C_4$alkyl and methoxy, and the other of $R^1$ to $R^8$ are H, with the proviso that $R^2$, $R^3$, $R^6$ and $R^7$ are neither -F nor methyl, and where $R^9$ and $R^{10}$ are defined as above, or (d) two pairs of adjacent radicals or $R^1$ to $R^8$ are -CO-O-CO- or -CO-$NR^9$-CO-, at least one further radical of $R^1$ to $R^8$ is a substitutent selected from -$COOR^9$, -$CONR^9R^{10}$ and the groups a1, a2 and a3, including $C_1$-$C_4$alkyl and methoxy, and the other radicals of $R^1$ to $R^8$ are H, and where $R^9$ and $R^{10}$ are as defined above.

2. A compound according to claim 1, in which $R^1$, $R^4$, $R^5$ and $R^8$ are H.

3. A compound according to claim 1, in which $R^6$ is said substituent and $R^1$ to $R^5$, $R^7$ and $R^8$ are H, or $R^7$ is said substituent and $R^1$ to $R^5$ and $R^8$ are H.

4. A compound according to claim 1, in which $R^6$ and $R^2$ are said substituent and $R^1$, $R^3$ to $R^5$, $R^7$ and $R^8$ are H, or $R^6$, $R^2$ and $R^3$ are said substituent and $R^1$, $R^4$, $R^5$, $R^7$ and $R^8$ are H, or $R^6$, $R^7$ and $R^2$ are said substituent and $R^1$, $R^3$ to $R^5$ and $R^8$ are H, or $R^6$, $R^7$, $R^2$ and $R^3$ are said substituent and $R^1$, $R^4$, $R^5$ and $R^8$ are H.

5. A compound according to claim 1, in which (a) $R^1$, $R^2$, $R^3$ and $R^4$ are H and at least one of the radicals $R^5$ to $R^8$ independently is a substituent as defined herein and the other radicals $R^5$ to $R^8$ are H, the substituent being selected from the group consisting of a1 and a2:

(a1) $C_1$-$C_{18}$-alkyl$(X)_{\overline{p}}$, $C_3$-$C_{12}$alkenyl$(X)_{\overline{p}}$, $C_3$-$C_{12}$alkynyl$(X)_{\overline{p}}$, $C_5$cycloalkoxy$(X)_p$, $C_6$-cycloalkyl-$(X)_{\overline{p}}$, ($C_1$-$C_6$alkyl)-$C_5$cycloalkyl$(X)_{\overline{p}}$, ($C_1$-$C_6$alkyl)-$C_6$cycloalkyl$(X)_{\overline{p}}$, $C_5$cycloalkyl-$CH_2(X)_{\overline{p}}$, $C_6$cycloalkly-$CH_2(X)_{\overline{p}}$, ($C_1$-$C_6$alkyl)-$C_5$cycloalkyl-$CH_2(X)_{\overline{p}}$, ($C_1$-$C_6$alkyl)-$C_6$cycloalkyl-$CH_2(X)_{\overline{p}}$, phenyl$(X)_{\overline{p}}$, ($C_1$-$C_6$alkyl)-phenyl$(X)_{\overline{p}}$, benzyl$(X)_{\overline{p}}$ or ($C_1$-$C_6$alkyl)-benzyl$(X)_{\overline{p}}$, each of which is unsubstituted or substituted by -F, -Cl, -CN, -$CONR^9R^{10}$, -$OR^9$, -$SR^9$ or -$COOR^9$; X is -O-, -S-, -SO- or -$SO_2$- and p is 0 or 1; and (a2) -$CF_3$, -CN, -Si($C_1$alkyl or $C_2$alkyl)$_3$, -S-$(C_mH_{2m}\text{-}O)_{\overline{n}}R^{11}$ or -O-$(C_mH_{2m}\text{-}O)_{\overline{n}}R^{11}$; or (b) $R^1$, $R^2$, $R^3$ and $R^4$ are H, at least one of $R^5$ to $R^8$ is -F or -Cl, at least one further member of $R^5$ to $R^8$ are a substituent from groups a1 and a2 above including $C_1$-$C_4$alkyl and methoxy, and the other members of $R^5$ to $R^8$ are H; and $R^9$ and $R^{10}$ independently of one another are H, $C_1$-$C_6$alkyl or -$CH_2CH_2OH$, or $R^9$ and $R^{10}$ together are tetramethylene, pentamethylene or -$CH_2CH_2NR^9CH_2CH_2$-; $R^{11}$ is H or $C_1$-$C_4$alkyl; and m is 2 or 3 and n is a number from 2 to 12.

6. A compound according to claim 1, in which p is 1.

7. A compound according to claim 5, in which $R^1$ to $R^5$, $R^7$ and $R^8$ are H and $R^6$ is a substituent as defined herein or $R^1$ to $R^5$ and $R^8$ are H and $R^6$ and $R^7$ are a substituent as defined herein, the substituent being selected from the group consisting of -Si($CH_3$)$_3$; -$CF_3$; -CN; $C_1$-$C_6$alkyl or benzyl, each of which is substituted by -$COOR^9$; $C_1$-$C_{18}$alkoxy or $C_1$-$C_{18}$alkylthio each of which is unsubstituted or substituted by -OH; phenyl-X-, benzyl-X-, $C_1$-$C_4$alkylphenyl-X- or $C_1$-$C_4$alkylbenzyl-X-, each of which is unsubstituted or substituted by -F, -Cl, -OH, $C_1$-$C_4$alkoxy or $C_1$-$C_4$alkylthio and in which X is -O-, -S- or -$SO_2$-; or unsubstituted $C_3$-$C_{12}$alkenyloxy.

8. A compound according to claim 1, in which $R^1$, $R^4$, $R^5$ and $R^8$ and H and at least one of $R^2$ and $R^3$ is a substituent as defined herein and the other is H, at least one of $R^6$ and $R^7$ is a substituent as defined herein, and the other is H, the substituent being selected from the group consisting of -$COOR^9$, -$CONR^9R^{10}$ or $C_1$-$C_{18}$alkyl$(X)_{\overline{p}}$, $C_3$-$C_{12}$alkenyl$(X)_{\overline{p}}$, $C_3$-$C_{12}$alkynyl$(X)_{\overline{p}}$, $C_5$cycloalkyl$(X)_{\overline{p}}$, $C_6$-cycloalkyl$(X)_{\overline{p}}$, ($C_1$-$C_6$alkyl)-$C_5$cycloalkyl$(X)_{\overline{p}}$, ($C_1$-$C_6$alkyl)-$C_6$cycloalkyl$(X)_{\overline{p}}$, $C_5$cycloalkyl-$CH_2(X)_{\overline{p}}$, $C_6$-cycloalkyl-$CH_2(X)_{\overline{p}}$, ($C_1$-$C_6$alkyl)-$C_5$cycloalkyl-$CH_2$-$X)_{\overline{p}}$, ($C_1$-$C_6$alkyl)-$C_6$cycloalkyl-$CH_2$-$X)_{\overline{p}}$, phenyl$(X)_p$, ($C_1$-$C_6$alkyl)-phenyl$(X)_{\overline{p}}$, benzyl-$(X)_{\overline{p}}$ or ($C_1$-$C_6$alkyl)-benzyl$(X)_{\overline{p}}$, each of which is unsubstituted or substituted by -F, -Cl, -CN, -$NR^9R^{10}$, -$OR^9$, -$SR^9$ or -$COOR^9$; X is -O-, -S-, -SO- or -$SO_2$- and p is 0 or 1; or selected from the group consisting of -$CF_3$ -CN, -Si($C_1$alkyl or $C_2$alkyl)$_3$, -S$(C_mH_{2m}O)_{\overline{n}}R^{11}$ or -O-$(C_mH_{2m}\text{-}O)_{\overline{n}}R^{11}$; or $R^2$ and $R^3$ together are -CO-O-CO- or -CO-$NR^9$-CO-; and at least one of $R^6$ and $R^7$ is one of the substituents defined above and the other is H, or $R^6$ and $R^7$ together are -CO-O-CO- or -CO-$NR^9$-CO-; $R^9$ and $R^{10}$ independently of one another are H, $C_1$-$C_6$alkyl or -$CH_2CH_2OH$, or $R^9$ and $R^{10}$ together are tetramethylene, pentamethylene or -$CH_2CH_2NR^9CH_2CH_2$-; $R^{11}$ is H or $C_1$-$C_4$alkyl; and m is 2 or 3 and n is a number from 2 to 12.

9. A compound according to claim 8, in which p is 1.

10. A compound according to claim 8, in which the substituent is selected from the group consisting of -$COOR^9$; -Si($CH_3$)$_3$; -$CH_3$; -CN; $C_1$-$C_6$-alkyl or benzyl each of which is substituted by -$COOR^9$; $C_1$-$C_{18}$alkoxy or $C_1$-$C_{18}$alkylthio each of which is unsubstituted or substituted by -OH; phenyl-X-, benzyl-X-, $C_1$-$C_4$alkylphenyl-X- or $C_1$-$C_4$alkylbenzyl-X-, each of which is unsubstituted or substituted by -F, -Cl, -OH, $C_1$-$C_4$alkoxy or $C_1$-$C_4$alkylthio and in which X is -O-, -S- or -$SO_2$-; or unsubstituted $C_3$-$C_{12}$alkenyloxy.

11. A compound according to claim 8, in which the substituent is selected from the group -$CF_3$, $C_1$-$C_{18}$alkoxy and -$COOR^9$.

12. A compound according to claim 5, in which p is 1.

* * * * *